United States Patent
Kang

(10) Patent No.: US 8,611,588 B2
(45) Date of Patent: Dec. 17, 2013

(54) METHOD OF MEASURING PROGRESS OF ALOPECIA

(76) Inventor: Jin Soo Kang, Seoul (KR)

( * ) Notice: Subject to any disclaimer, the term of this patent is extended or adjusted under 35 U.S.C. 154(b) by 369 days.

(21) Appl. No.: 13/151,615

(22) Filed: Jun. 2, 2011

(65) Prior Publication Data

US 2012/0250958 A1 Oct. 4, 2012

(30) Foreign Application Priority Data

Mar. 29, 2011 (KR) .................. 10-2011-0028369

(51) Int. Cl.
*G06K 9/00* (2006.01)

(52) U.S. Cl.
USPC .......................................... 382/100; 382/128

(58) Field of Classification Search
USPC .......................................... 382/100, 128–134
See application file for complete search history.

(56) References Cited

U.S. PATENT DOCUMENTS

| | | | | |
|---|---|---|---|---|
| 5,060,171 | A * | 10/1991 | Steir et al. | 345/630 |
| 5,335,293 | A * | 8/1994 | Vannelli et al. | 382/110 |
| 7,212,672 | B2 * | 5/2007 | Fujieda et al. | 382/199 |
| 7,627,157 | B2 * | 12/2009 | Qureshi et al. | 382/128 |
| 7,634,103 | B2 * | 12/2009 | Rubinstenn et al. | 382/100 |
| 8,115,807 | B2 * | 2/2012 | Rassman et al. | 348/77 |
| 8,428,382 | B2 * | 4/2013 | Sato | 382/254 |
| 2001/0006555 | A1 * | 7/2001 | Loussouarn et al. | 382/128 |
| 2001/0017936 | A1 * | 8/2001 | Loussouarn et al. | 382/128 |
| 2004/0095359 | A1 * | 5/2004 | Simon et al. | 345/619 |
| 2004/0145656 | A1 * | 7/2004 | Betra | 348/77 |
| 2004/0202631 | A1 * | 10/2004 | Hirata et al. | 424/70.1 |
| 2007/0242858 | A1 * | 10/2007 | Aradhye et al. | 382/115 |
| 2008/0216334 | A1 * | 9/2008 | Pak et al. | 33/512 |
| 2011/0299776 | A1 * | 12/2011 | Lee et al. | 382/173 |
| 2012/0250958 | A1 * | 10/2012 | Kang | 382/128 |

* cited by examiner

*Primary Examiner* — Alex Liew
(74) *Attorney, Agent, or Firm* — Kile Park Reed & Houtteman PLLC

(57) ABSTRACT

Disclosed herein is a method of measuring the progress of alopecia in which the progress of alopecia of a hair loss region of a measured person is accurately determined through a mathematical algorithm. In the method, a value indicating the progress of alopecia of the hair loss region is numerically calculated based on the numbers of hairs, thicknesses of the hairs and the numbers of the hairs of a normal region and a hair loss region of the measured person, thereby more accurately determining the progress of alopecia compared to a conventional method of measuring the progress of alopecia from the observation with the naked eye and the experience of a measurer. Further, the progress of alopecia is accurately determined, and thus a proper treatment is carried out according to the progress of alopecia, thus effectively treating alopecia.

4 Claims, 6 Drawing Sheets

METHOD OF MEASURING PROGRESS OF ALOPECIA

BACKGROUND OF THE INVENTION

1. Field of the Invention

The present invention relates to a method of measuring the progress of alopecia, and more particularly to a method of measuring the progress of alopecia in which the progress of alopecia is accurately determined through a mathematical algorithm.

2. Description of the Related Art

In general, alopecia refers to a state in which hairs are not present in regions which should have hair, and more particularly to loss of terminal hairs (thick and black hairs) from the scalp. Loss of the terminal hairs may cause cosmetic problems, differing from colorless and thin vellus hairs. Koreans having a lower density of hairs than Westerners generally have about 50,000 to 70,000 hairs, and normally lose about 50 to 70 hairs per day.

However, if more than 100 hairs are lost per day, there is a strong possibility of alopecia, and if a person is diagnosed with alopecia, the person needs to receive proper treatment according to the progress of alopecia so as to effectively treat alopecia.

That is, in order to properly treat alopecia according to the progress of alopecia, it is important to measure the progress of alopecia. For this purpose, a measurer conventionally measures the progress of alopecia by checking hair states of a normal region and a hair loss region with the naked eye.

However, in such a method, since the progress of alopecia is determined based upon observation with the naked eye and the experience of the measurer, accuracy in determining the progress of alopecia is greatly lowered and thus proper alopecia treatment is not carried out, thereby causing a difficulty in effectively treating alopecia.

SUMMARY OF THE INVENTION

Therefore, the present invention has been made in view of the above problems, and it is an object of the present invention to provide a method of measuring the progress of alopecia in which the progress of alopecia is accurately determined through a mathematical algorithm.

In accordance with an aspect of the present invention, the above and other objects can be accomplished by the provision of a method of measuring the progress of alopecia including detecting the number of hairs based on a photographed image of a hair state of a normal region, calculating the mean thickness of the hairs based on the photographed image of the hair state of the normal region, detecting the number of hairs based on a photographed image of a hair state of a hair loss region, calculating the mean thickness of the hairs based on the photographed image of the hair state of the hair loss region, and calculating a value indicating the progress of alopecia of the hair loss region based on the number and the mean thickness of the hairs of the normal region and the number and the mean thickness of the hairs of the hair loss region.

The calculation of the value indicating the progress of alopecia of the hair loss region may be carried out according to Equation below, $$HLP = \frac{(H_N - H_L)}{H_N} \times 100 + H_L \times \frac{(D_N - D_L)}{D_N} \times \frac{1}{H_N} \times 100,$$

here, HLP may be the value indicating the progress of alopecia, $H_N$ may be the number of the hairs of the normal region, $H_L$ may be the number of the hairs of the hair loss region, $D_N$ may be the mean thickness of the hairs of the normal region and $D_L$ may be the mean thickness of the hairs of the hair loss region.

In accordance with another aspect of the present invention, there is provided a method of measuring the progress of alopecia including detecting the number of hair follicles based on a photographed image of a hair state of a normal region, calculating the mean thickness of hairs based on the photographed image of the hair state of the normal region, detecting the number of hair follicles, each of which has one hair, and the number of vacant hair follicles based on a photographed image of a hair state of a hair loss region, detecting the number of hairs, each of which has a thickness less than ½ of the mean thickness of the hairs of the normal region based on the photographed image of the hair state of the hair loss region, and calculating a value indicating the progress of alopecia of the hair loss region based on the number of the hair follicles of the normal region, the number of the hair follicles of the hair loss region, each of which has one hair, the number of the vacant hair follicles of the hair loss region, and the number of the hairs, each of which has a thickness less than ½ of the mean thickness of the hairs of the normal region.

The calculation of the value indicating the progress of alopecia of the hair loss region may be carried out according to Equation below, $$HLP' = \frac{\left(F_1 + 2 \times F_0 + \frac{1}{2} \times H_{1/2}\right)}{(2 \times F_N)} \times 100$$

here, HLP' may be the value indicating the progress of alopecia, $F_N$ may be the number of the hair follicles of the normal region, $F_1$ may be the number of the hair follicles of the hair loss region, each of which has one hair, $F_0$ may be the number of the vacant hair follicles of the hair loss region, and $H_{1/2}$ may be the number of the hairs of the hair loss region, each of which has a thickness less than ½ of the mean thickness of the hairs of the normal region.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
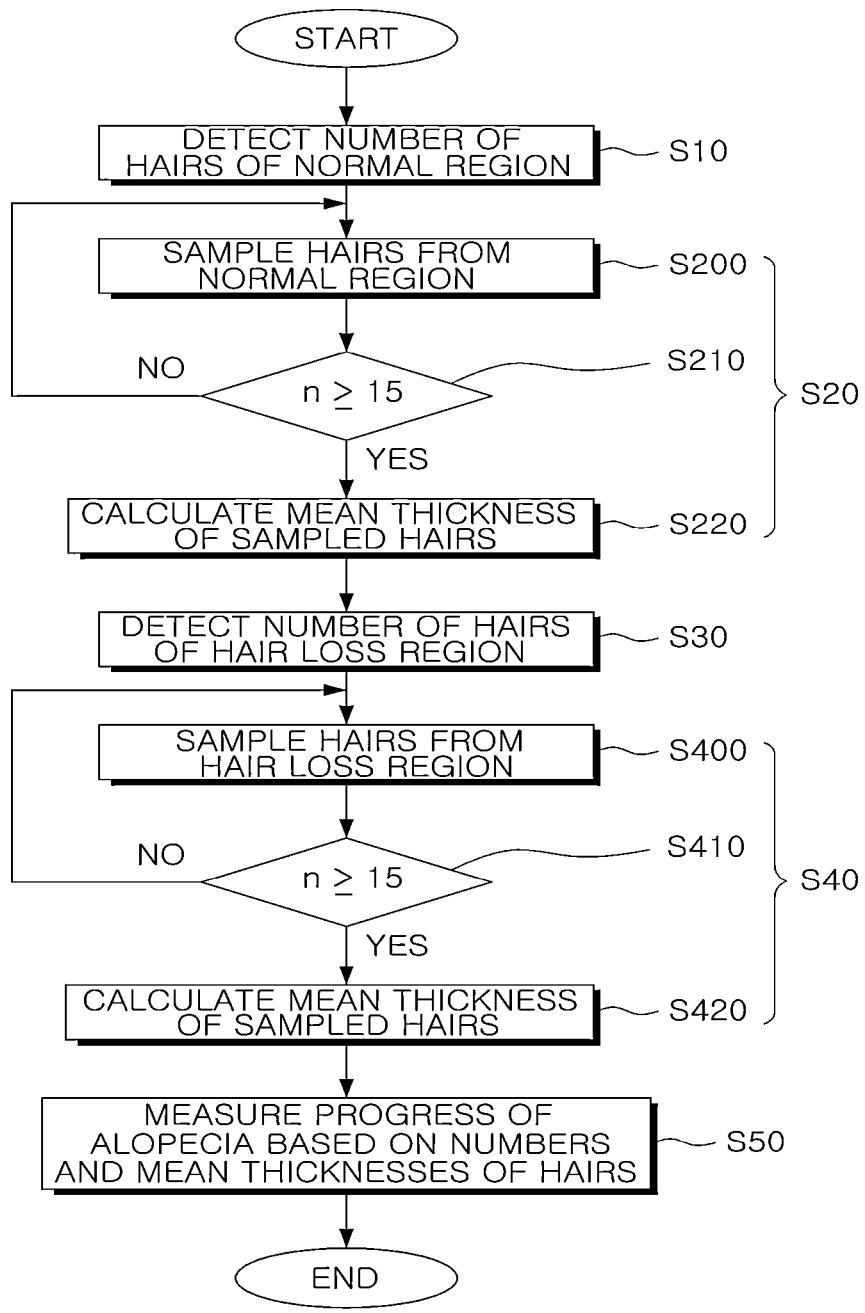
FIG. 1 is a flow chart illustrating a method of measuring the progress of alopecia in accordance with one embodiment of the present invention.

Now, preferred embodiments of the present invention will be described in detail with reference to the annexed drawings so that those skilled in the art may easily embody the present invention. However, the present invention may be variously modified and is not limited to the embodiments. Further, in the drawings, parts which do not relate to the following description will be omitted, and the same or similar elements are denoted by the same reference numerals even though they are depicted in different drawings.

Further, if a part "includes" elements in the following description, it means that the part does not exclude other elements but may include these elements unless stated otherwise.

Figure 3:
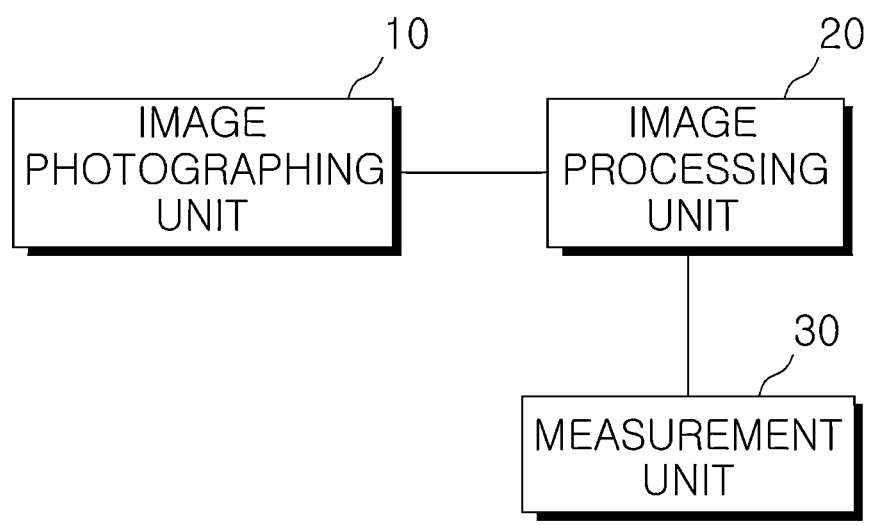
FIG. 3 is a block diagram illustrating a system to measure the progress of alopecia.
Figure 4A:
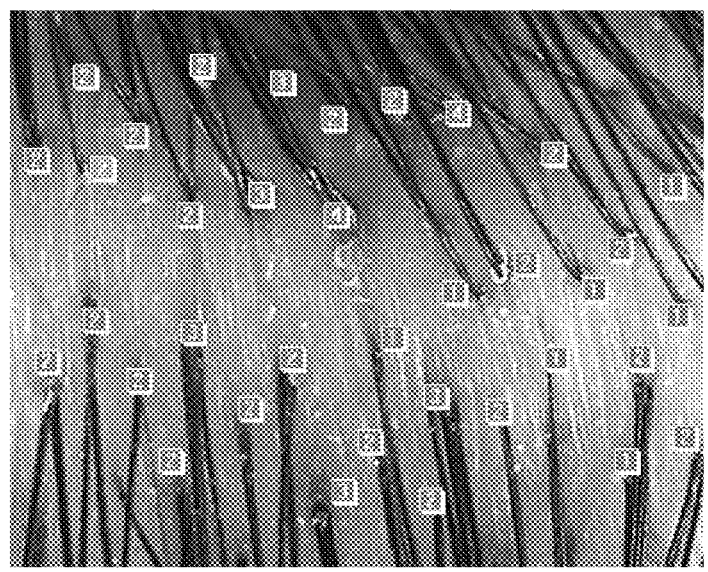
FIG. 4A is a photograph illustrating detection of the number of hairs in a normal region.
Figure 4B:
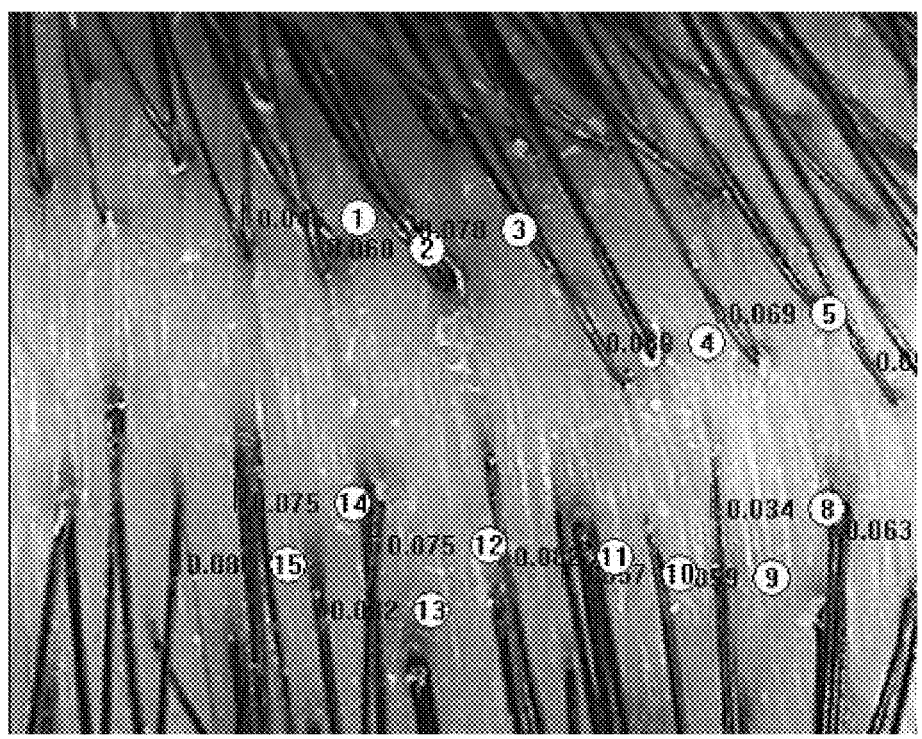
FIG. 4B is a photograph illustrating calculation of thicknesses of the hairs in the normal region.
Figure 5A:
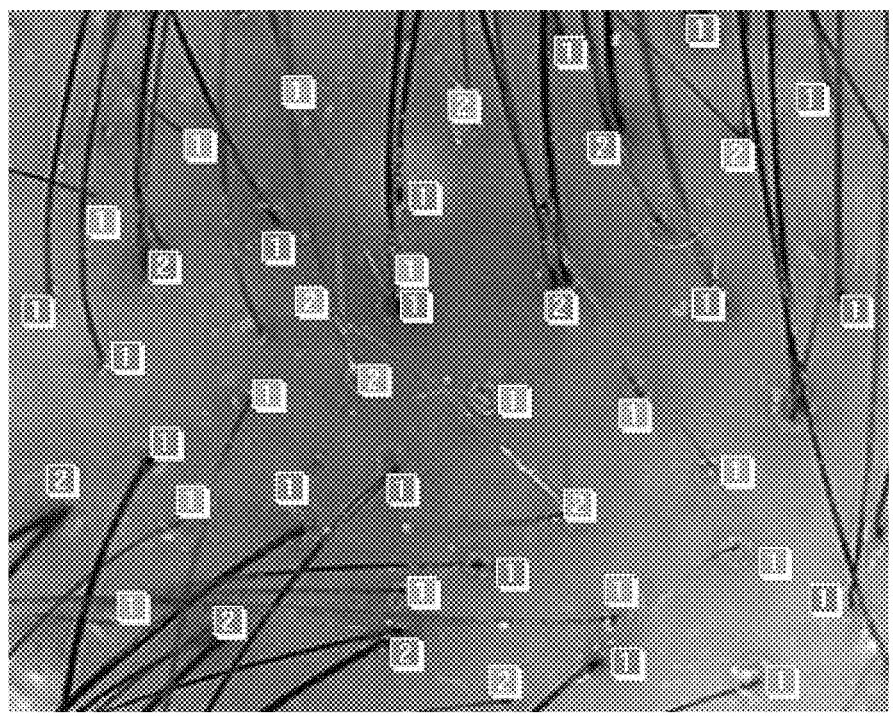
FIG. 5A is a photograph illustrating detection of the number of hairs in a hair loss region.
Figure 5B:
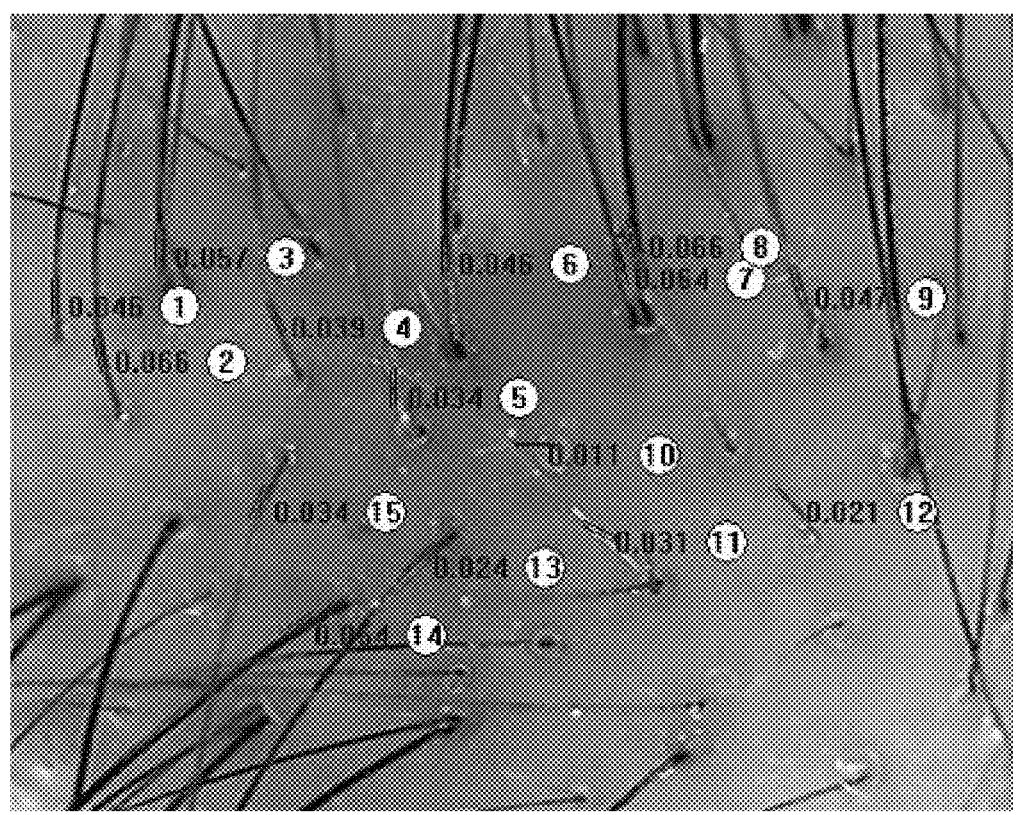
FIG. 5B is a photograph illustrating calculation of thicknesses of the hairs in the hair loss region.

FIG. 3 is a block diagram illustrating a system to measure the progress of alopecia. Such a system includes an image photographing unit 10, an image processing unit 20 and a measurement unit 30. The image photographing unit 10 photographs images of a normal region and a hair loss region of a measured person, and the image processing unit 20 detects the number and mean thickness of the hairs and the number of hair follicles in the normal region and the number and mean thickness of hairs and the number of hair follicles in the hair loss region based on the images photographed by the image photographing unit 10. The measurement unit 30 measures the progress of alopecia through a mathematical algorithm based on the numbers and mean thicknesses of hairs and the numbers of hair follicles detected by the image processing unit 20.

FIG. 1 is a flow chart illustrating a method of measuring the progress of alopecia in accordance with one embodiment of the present invention. The method in accordance with this embodiment includes detecting the number $H_N$ of hairs based on a photographed image of a hair state of a normal region (Operation S10), calculating the mean thickness $D_N$ of the hairs based on the photographed image of the hair state of the normal region (Operation S20), detecting the number $H_L$ of hairs based on a photographed image of a hair state of a hair loss region (Operation S30), calculating the mean thickness $D_L$ of the hairs based on the photographed image of the hair state of the hair loss region (Operation S40), and calculating a value HLP indicating the progress of alopecia of the hair loss region based on the number $H_N$ and the mean thickness $D_N$ of the hairs of the normal region and the number $H_L$ and the mean thickness $D_L$ of the hairs of the hair loss region (Operation S50).

In Operation S10, the number $H_N$ of the hairs of the normal region is detected. More concretely, the hairs are discriminated from the scalp through a brightness recognition or color recognition process based on the photographed image of the hair state of the normal region, and the number $H_N$ of the hairs of the normal region is detected from the discriminated hairs. That is, since there is a sharp contrast between the hairs and the scalp, the hairs are clearly discriminated from the scalp and the hairs are clearly discriminated from one another within the image. Therefore, the number $H_N$ of the hairs of the normal region is detected by counting the hairs of the normal region based on the photographed image.

In Operation S20, the mean thickness $D_N$ of the hairs of the normal region is calculated. More concretely, thicknesses of the respective hairs are calculated based on the image having passed through the brightness recognition or color recognition process in Operation S10, and the mean of the thicknesses is calculated, thus calculating the mean thickness $D_N$ of the hairs of the normal region. That is, since there is a sharp contrast between the hairs and the scalp, the hairs are clearly discriminated from the scalp and the hairs are clearly discriminated from one another within the image. Therefore, the thicknesses of the respective hairs are detected based on the photographed image, and the mean of the thicknesses is calculated, thus calculating the mean thickness $D_N$ of the hairs of the normal region.

Further, Operation S20 may include sampling hairs from the normal region (Operation S200), checking the number of the sampled hairs (Operation S210), and calculating the mean thickness $D_N$ of the sampled hairs (Operation S220). That is, calculation of the mean thickness $D_N$ of the hairs of the normal region by detecting thicknesses of all the hairs present in the photographed image of the hair state of the normal region requires a long time due to considerable data throughput. Therefore, a proper number of hairs are sampled from the normal region and then the mean thickness $D_N$ of the sampled hairs is calculated.

In Operation S200, hairs are sampled from the normal region. More concretely, hairs are randomly sampled from the photographed image of the hair state of the normal region. Here, in order to reduce an error of the mean thickness $D_N$ of the hairs, at least 15 hairs are preferably sampled from the photographed image.

In Operation S210, the number of the sampled hairs is checked. If the number of the hairs sampled during Operation S200 is below 15, Operation S200 is repeated, and if the number of the sampled hairs exceeds 15, Operation S220 is carried out.

In Operation S220, the mean thickness $D_N$ of the sampled hairs is calculated. More concretely, thicknesses of the respective sampled hairs are detected and the mean of the thicknesses is calculated, thus calculating the mean thickness $D_N$ of the sampled hairs. Here, the thicknesses of the sampled hairs are detected based on the image having passed through the brightness recognition or color recognition process.

In Operation S30, the number $H_L$ of the hairs of the hair loss region is detected. More concretely, the hairs are discriminated from the scalp through the brightness recognition or color recognition process based on the photographed image of the hair state of the hair loss region, and the number $H_L$ of the hairs of the hair loss region is detected from the discriminated hairs. That is, since there is a sharp contrast between the hairs and the scalp, the hairs are clearly discriminated from the scalp and the hairs are clearly discriminated from one another within the image. Therefore, the number $H_L$ of the hairs of the hair loss region is detected by counting the hairs of the hair loss region based on the photographed image.

In Operation S40, the mean thickness $D_L$ of the hairs of the hair loss region is calculated. More concretely, thicknesses of the respective hairs are calculated based on the image having passed through the brightness recognition or color recognition process, and the mean of the thicknesses is calculated, thus calculating the mean thickness $D_L$ of the hairs of the hair loss region. That is, since there is a sharp contrast between the hairs and the scalp, the hairs are clearly discriminated from the scalp and the hairs are clearly discriminated from one another within the image. Therefore, the thicknesses of the respective hairs are detected based on the photographed image, and then the mean of the thicknesses is calculated, thus calculating the mean thickness $D_L$ of the hairs of the hair loss region.

Further, Operation S40 may include sampling hairs from the hair loss region (Operation S400), checking the number of the sampled hairs (Operation S410), and calculating the mean thickness $D_L$ of the sampled hairs (Operation S420). That is, calculation of the mean thickness $D_L$ of the hairs of the hair loss region by detecting thicknesses of all the hairs present in the photographed image of the hair state of the hair loss region requires a long time due to considerable data throughput. Therefore, a proper number of hairs are sampled from the hair loss region and then the mean thickness $D_L$ of the sampled hairs is calculated.

In Operation S400, hairs are sampled from the hair loss region. More concretely, hairs are randomly sampled from the photographed image of the hair state of the hair loss region. Here, in order to reduce an error of the mean thickness $D_L$ of the hairs, at least 15 hairs are preferably sampled from the photographed image.

In Operation S410, the number of the sampled hairs is checked. If the number of the hairs sampled during Operation S400 is below 15, Operation S400 is repeated, and if the number of the sampled hairs exceeds 15, Operation S420 is carried out.

In Operation S420, the mean thickness $D_L$ of the sampled hairs is calculated. More concretely, thicknesses of the respective sampled hairs are detected and the mean of the thicknesses is calculated, thus calculating the mean thickness $D_L$ of the sampled hairs. Here, the thicknesses of the sampled hairs are detected based on the image having passed through the brightness recognition or color recognition process.

In Operation S50, the value HLP indicating the progress of alopecia of the hair loss region is calculated. More concretely, the number $H_N$ of the hairs of the normal region detected in Operation S10, the mean thickness $D_N$ of the hairs of the normal region calculated in Operation S20, the number $H_L$ of the hairs of the hair loss region detected in Operation S30 and the mean thickness $D_L$ of the hairs of the hair loss region in Operation S40 are applied to Equation 1 below, thereby calculating the value HLP indicating the progress of alopecia of the hair loss region.

$$HLP = \frac{(H_N - H_L)}{H_N} \times 100 + H_L \times \frac{(D_N - D_L)}{D_N} \times \frac{1}{H_N} \times 100 \quad \text{[Equation 1]}$$

Here, HLP is a value indicating the progress of alopecia, $H_N$ is the number of hairs of a normal region, $H_L$ is the number of hairs of a hair loss region, $D_N$ is the mean thickness of the hairs of the normal region and $D_L$ is the mean thickness of the hairs of the hair loss region.

For example, with reference to FIGS. 4A and 4B and FIGS. 5A and 5B, the number $H_N$ of the hairs of the normal region is 74, the number $H_L$ of the hairs of the hair loss region is 54, the mean thickness $D_N$ of the hairs of the normal region is 0.067 cm and the mean thickness $D_L$ of the hairs of the hair loss region is 0.035 cm. In this case, according to Equation 1, the value HLP indicating the progress of alopecia of the hair loss region is 61.8%.

As the value HLP indicating the progress of alopecia of the hair loss region calculated by Equation 1 is large, it is understood that the hair loss region is in a serious alopecia state, and as the value HLP indicating the progress of alopecia of the hair loss region is small, it is understood than the hair loss region is in an initial alopecia state.

As described above, since the value HLP indicating the progress of alopecia is accurately calculated through a mathematical algorithm, a proper treatment may be carried out according to the calculated value HLP indicating the progress of alopecia, thus effectively treating alopecia.

Figure 2:
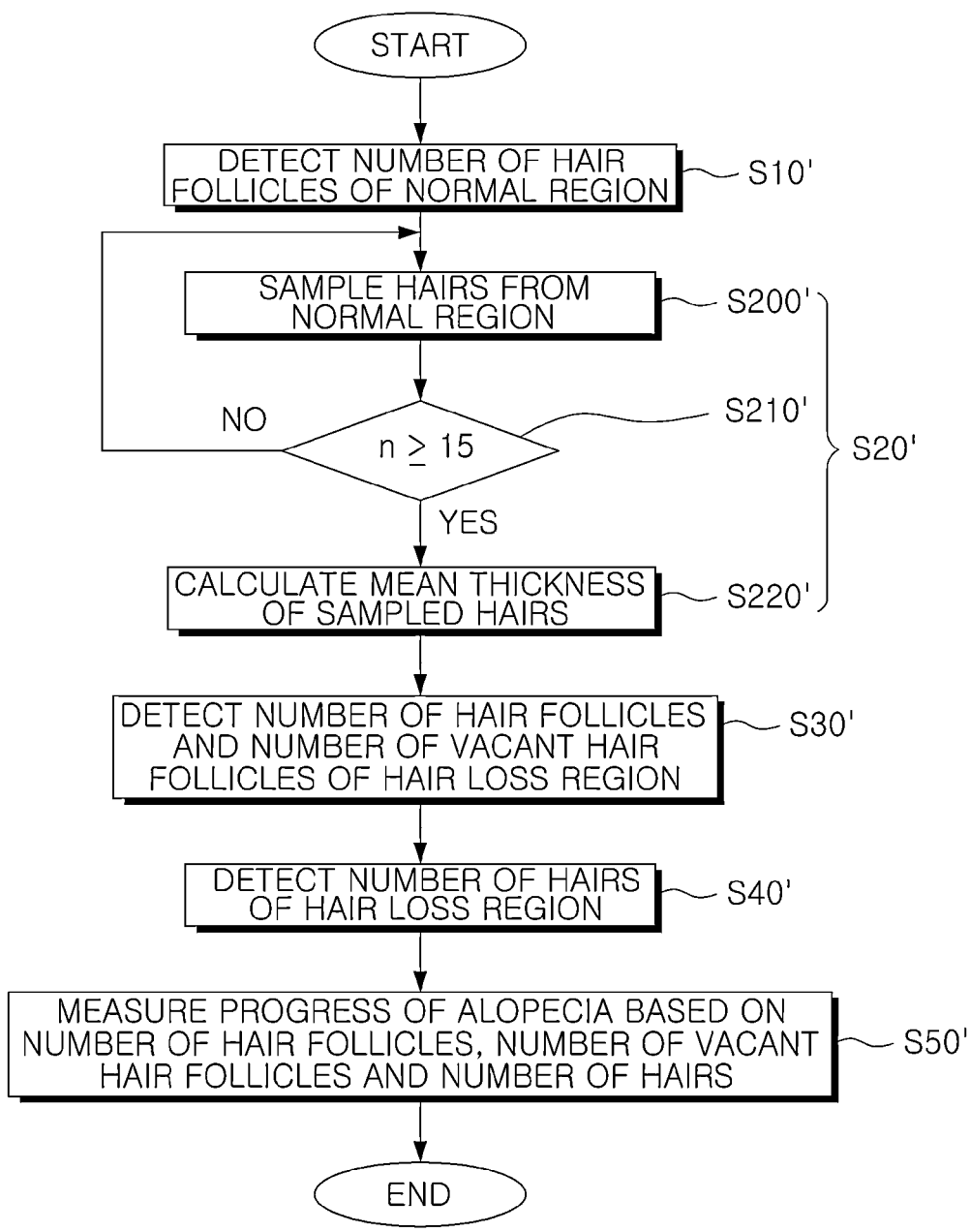
FIG. 2 is a flow chart illustrating a method of measuring the progress of alopecia in accordance with another embodiment of the present invention.

FIG. 2 is a flow chart illustrating a method of measuring the progress of alopecia in accordance with another embodiment of the present invention. The method in accordance with this embodiment includes detecting the number $F_N$ of hair follicles based on a photographed image of a hair state of a normal region (Operation S10'), calculating the mean thickness $D_N$ of hairs based on the photographed image of the hair state of the normal region (Operation S20'), detecting the number $F_1$ of hair follicles, each of which has one hair, and the number $F_0$ of vacant hair follicles based on a photographed image of a hair state of a hair loss region (Operation S30'), detecting the number $H_{1/2}$ of hairs, each of which has a thickness less than ½ of the mean thickness $D_N$ of the hairs of the normal region based on the photographed image of the hair state of the hair loss region (Operation S40'), and calculating a value HLP' indicating the progress of alopecia of the hair loss region based on the number $F_N$ of the hair follicles of the normal region, the number $F_1$ of the hair follicles of the hair loss region, each of which has one hair, the number $F_0$ of the vacant hair follicles of the hair loss region, and the number $H_{1/2}$ of the hairs, each of which has a thickness less than ½ of the mean thickness of the hairs of the normal region.

In Operation S10', the number $F_N$ of the hair follicles of the normal region is detected. More concretely, the hairs are discriminated from the scalp through a brightness recognition or color recognition process based on the photographed image of the hair state of the normal region, and the number $F_N$ of the hair follicles of the normal region is detected from the discriminated hairs. That is, since there is a sharp contrast between the hairs and the scalp, the hairs are clearly discriminated from the scalp and the hairs are clearly discriminated from one another within the image. Therefore, the number $F_N$ of the hair follicles of the normal region is detected by counting ends of the hairs of the normal region.

In Operation S20', the mean thickness $D_N$ of the hairs of the normal region is calculated. More concretely, thicknesses of the respective hairs are calculated based on the image having passed through the brightness recognition or color recognition process in Operation S10', and the mean of the thicknesses is calculated, thus calculating the mean thickness $D_N$ of the hairs of the normal region. That is, since there is a sharp contrast between the hairs and the scalp, the hairs are clearly discriminated from the scalp and the hairs are clearly discriminated from one another within the image. Therefore, the thicknesses of the respective hairs are detected based on the photographed image, and the mean of the thicknesses is calculated, thus calculating the mean thickness $D_N$ of the hairs of the normal region.

Further, Operation S20' may include sampling hairs from the normal region (Operation S200'), checking the number of the sampled hairs (Operation S210'), and calculating the mean thickness $D_N$ of the sampled hairs (Operation S220'). That is, calculation of the mean thickness $D_N$ of the hairs of the normal region by detecting thicknesses of all the hairs present in the photographed image of the hair state of the normal region requires a long time due to considerable data throughput. Therefore, a proper number of hairs are sampled from the normal region and then the mean thickness $D_N$ of the sampled hairs is calculated.

In Operation S200', hairs are sampled from the normal region. More concretely, hairs are randomly sampled from the photographed image of the hair state of the normal region. Here, in order to reduce an error of the mean thickness $D_N$ of the hairs, at least 15 hairs are preferably sampled from the photographed image.

In Operation S210', the number of the sampled hairs is checked. If the number of the hairs sampled during Operation S200' is below 15, Operation S200' is repeated, and if the number of the sampled hairs exceeds 15, Operation S220' is carried out.

In Operation S220', the mean thickness $D_N$ of the sampled hairs is calculated. More concretely, thicknesses of the respective sampled hairs are detected and the mean of the thicknesses is calculated, thus calculating the mean thickness $D_N$ of the sampled hairs. Here, the thicknesses of the sampled hairs are detected based on the image having passed through the brightness recognition or color recognition process.

In Operation S30', the number $F_1$ of the hair follicles, each of which has one hair, and the number $F_0$ of the vacant hair follicles are detected. More concretely, the hairs are discriminated from the scalp through the brightness recognition or color recognition process based on the photographed image of the hair state of the hair loss region, and the number $F_1$ of the hair follicles, each of which has one hair, and the number $F_0$ of the vacant hair follicles are detected from the discriminated hairs. That is, since there is a sharp contrast between the hairs and the scalp, the hairs are clearly discriminated from the scalp and the hairs are clearly discriminated from one another within the image. Therefore, the number $F_1$ of the hair follicles, each of which has one hair, and the number $F_0$ of the vacant hair follicles are detected by counting ends of respective hairs of the hair loss region and the hairs connected to the ends.

In operation S40', the number $H_{1/2}$ of the hairs of the hair loss region, each of which has a thickness less than ½ of the mean thickness $D_N$ of the hairs of the normal region, is detected. More concretely, thicknesses of the respective hairs are detected based on the image having passed through the brightness recognition or color recognition process in Operation S30', and are compared with the mean thickness $D_N$ of the hairs of the normal region calculated in Operation S20', thus detecting the number $H_{1/2}$ of the hairs of the hair loss region, each of which has a thickness less than ½ of the mean thickness $D_N$ of the hairs of the normal region.

In Operation S50', the value HLP' indicating the progress of alopecia of the hair loss region is calculated. More concretely, the number $F_N$ of the hair follicles of the normal region detected in Operation S10', the number $F_1$ of the hair follicles of the hair loss region, each of which has one hair and the number $F_0$ of the vacant hair follicles of the hair loss region detected in Operation S30', and the number $H_{1/2}$ of the hairs of the hair loss region, each of which has a thickness less than ½ of the mean thickness $D_N$ of the hairs of the normal region, detected in Operation S40' are applied to Equation 2 below, thereby calculating the value HLP' indicating the progress of alopecia of the hair loss region.

$$HLP' = \frac{\left(F_1 + 2 \times F_0 + \frac{1}{2} \times H_{1/2}\right)}{(2 \times F_N)} \times 100 \quad \text{[Equation 2]}$$

Here, HLP' is a value indicating the progress of alopecia, $F_N$ is the number of hair follicles of a normal region, $F_1$ is the number of hair follicles of a hair loss region, each of which has one hair, $F_0$ is the number of vacant hair follicles of the hair loss region, and $H_{1/2}$ is the number of hairs of the hair loss region, each of which has a thickness less than ½ of the mean thickness of the hairs of the normal region.

For example, if the number $F_N$ of the hair follicles of the normal region is 36, the number of $F_1$ of the hair follicles of the hair loss region, each of which has one hair, is 30, the number $F_0$ of the vacant hair follicles of the hair loss region is 0, and the number $H_{1/2}$ of the hairs of the hair loss region, each of which has a thickness less than ½ of the mean thickness of the hairs of the normal region, is 26, the value HLP' indicating the progress of alopecia of the hair loss region according to Equation 2 is 59.7%.

As the value HLP' indicating the progress of alopecia of the hair loss region calculated by Equation 2 is large, it is understood that the hair loss region is in a serious alopecia state, and as the value HLP' indicating the progress of alopecia of the hair loss region is small, it is understood that the hair loss region is in an initial alopecia state.

As described, since the value HLP' indicating the progress of alopecia is accurately calculated through a mathematical algorithm, a proper treatment may be carried out according to the calculated value HLP' indicating the progress of alopecia, thus effectively treating alopecia.

As apparent from the above description, the present invention provides a method of measuring the progress of alopecia in which the progress of alopecia of a hair loss region of a measured person is numerically calculated through a mathematical algorithm based on the numbers of hairs, thicknesses of the hairs and the numbers of the hairs in a normal region and a hair loss region of the measured person, thereby more accurately determining the progress of alopecia compared to a conventional method of measuring the progress of alopecia from the observation with the naked eye and the experience of a measurer.

Further, the progress of alopecia is accurately determined, and thus a proper treatment is carried out according to the progress of alopecia, thus effectively treating alopecia.

The above-described embodiments of the present invention are not implemented only through devices and methods, but those skilled in the art will appreciate that the embodiments of the present invention may be implemented through programs performing functions corresponding to configurations of the embodiments of the present invention or media on which the programs are recorded.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of measuring the progress of alopecia comprising:
   detecting the number of hairs based on a photographed image of a hair state of a normal region;
   calculating the mean thickness of the hairs based on the photographed image of the hair state of the normal region;
   detecting the number of hairs based on a photographed image of a hair state of a hair loss region;
   calculating the mean thickness of the hairs based on the photographed image of the hair state of the hair loss region; and
   calculating a value indicating the progress of alopecia of the hair loss region based on the number and the mean thickness of the hairs of the normal region and the number and the mean thickness of the hairs of the hair loss region.

2. The method according to claim 1, wherein the calculation of the value indicating the progress of alopecia of the hair loss region is carried out according to Equation below, $$HLP = \frac{(H_N - H_L)}{H_N} \times 100 + H_L \times \frac{(D_N - D_L)}{D_N} \times \frac{1}{H_N} \times 100,$$

here, HLP is the value indicating the progress of alopecia, $H_N$ is the number of the hairs of the normal region, $H_L$ is the number of the hairs of the hair loss region, $D_N$ is the mean thickness of the hairs of the normal region and $D_L$ is the mean thickness of the hairs of the hair loss region.

3. A method of measuring the progress of alopecia comprising:

detecting the number of hair follicles based on a photographed image of a hair state of a normal region;

calculating the mean thickness of hairs based on the photographed image of the hair state of the normal region;

detecting the number of hair follicles, each of which has one hair, and the number of vacant hair follicles based on a photographed image of a hair state of a hair loss region;

detecting the number of hairs, each of which has a thickness less than ½ of the mean thickness of the hairs of the normal region based on the photographed image of the hair state of the hair loss region; and calculating a value indicating the progress of alopecia of the hair loss region based on the number of the hair follicles of the normal region, the number of the hair follicles of the hair loss region, each of which has one hair, the number of the vacant hair follicles of the hair loss region, and the number of the hairs, each of which has a thickness less than ½ of the mean thickness of the hairs of the normal region.

4. The method according to claim 3, wherein the calculation of the value indicating the progress of alopecia of the hair loss region is carried out according to Equation below, $$HLP' = \frac{\left(F_1 + 2 \times F_0 + \frac{1}{2} \times H_{1/2}\right)}{(2 \times F_N)} \times 100$$

here, HLP' is the value indicating the progress of alopecia, $F_N$ is the number of the hair follicles of the normal region, $F_1$ is the number of the hair follicles of the hair loss region, each of which has one hair, $F_0$ is the number of the vacant hair follicles of the hair loss region, and $H_{1/2}$ is the number of the hairs of the hair loss region, each of which has a thickness less than ½ of the mean thickness of the hairs of the normal region.

* * * * *